United States Patent
Laghi

(10) Patent No.: US 7,717,114 B1
(45) Date of Patent: May 18, 2010

(54) MASK SEAL INTERFACE

(75) Inventor: Aldo A. Laghi, Clearwater, FL (US)

(73) Assignee: Alps South, LLC, Clearwater, FL (US)

( * ) Notice: Subject to any disclaimer, the term of this patent is extended or adjusted under 35 U.S.C. 154(b) by 1565 days.

(21) Appl. No.: 10/711,868

(22) Filed: Oct. 11, 2004

(51) Int. Cl.
*A62B 18/08* (2006.01)

(52) U.S. Cl. .................... 128/206.12; 128/206.23; 128/206.24

(58) Field of Classification Search ............ 128/205.25, 128/205.29, 206.12, 206.14, 206.16, 206.18, 128/206.19, 206.21, 206.23, 206.24, 206.25, 128/206.27, 206.28, 207.11
See application file for complete search history.

(56) References Cited

U.S. PATENT DOCUMENTS

| | | | |
|---|---|---|---|
| 2,749,910 A | 6/1956 | Faulconer, Jr. | |
| 2,877,764 A | 3/1959 | Galleher, Jr. | |
| 2,917,045 A | 12/1959 | Schildknecht et al. | |
| 3,052,887 A | 9/1962 | Sockel et al. | |
| 4,022,200 A | 5/1977 | Jonson | |
| 4,369,284 A | 1/1983 | Chen | |
| 4,665,570 A | 5/1987 | Davis | |
| 5,370,688 A | 12/1994 | Schulz et al. | |
| 5,592,938 A | 1/1997 | Scarberry et al. | |
| 5,630,844 A | 5/1997 | Dogan et al. | |
| 5,710,206 A | 1/1998 | Francis et al. | |
| 5,760,117 A | 6/1998 | Chen | |
| 5,884,639 A | 3/1999 | Chen | |
| 5,962,572 A | 10/1999 | Chen | |
| 5,994,446 A | 11/1999 | Graulus et al. | |
| 5,994,450 A | 11/1999 | Pearce | |
| 6,117,176 A | 9/2000 | Chen | |
| 6,183,514 B1 | 2/2001 | Becker | |
| 6,324,703 B1 | 12/2001 | Chen | |
| 6,390,885 B1 | 5/2002 | Brooks | |
| 6,413,458 B1 | 7/2002 | Pearce | |
| 6,615,832 B1 | 9/2003 | Chen | |
| 6,631,718 B1 | 10/2003 | Lovell | |
| 6,672,548 B1 | 1/2004 | Yates | |
| 6,852,776 B2 | 2/2005 | Ong et al. | |
| 7,053,145 B1 | 5/2006 | Tasaka et al. | |
| 2002/0193878 A1 | 12/2002 | Bowman | |
| 2003/0122446 A1 | 7/2003 | Chen | |
| 2003/0195623 A1 | 10/2003 | Marchitto et al. | |
| 2003/0236313 A1 | 12/2003 | Pearce | |
| 2004/0068040 A1 | 4/2004 | Chen | |
| 2004/0070187 A1 | 4/2004 | Chen | |
| 2004/0072942 A1 | 4/2004 | Chen | |
| 2004/0073305 A1 | 4/2004 | Schneider-Nieskens | |
| 2004/0116591 A1 | 6/2004 | Chen | |
| 2005/0101693 A1 | 5/2005 | Arbogast et al. | |
| 2006/0020061 A1 | 1/2006 | Knoll et al. | |
| 2006/0076018 A1* | 4/2006 | Barnett et al. ......... | 128/206.24 |
| 2006/0231103 A1* | 10/2006 | Matula et al. ......... | 128/207.13 |

* cited by examiner

*Primary Examiner*—Peter D Mulcahy

(57) ABSTRACT

A face-seal interface for a respiratory mask utilizing an elastomer containing precipitated particles on its surface to provide a more comfortable long-term engagement with the skin of a wearer. A particle filled bladder forming the face-seal interface keeps a set shape and improves user comfort.

22 Claims, 11 Drawing Sheets

MASK SEAL INTERFACE

CROSS-REFERENCE TO RELATED APPLICATIONS

This application includes related subject matter to the subject matter in application Ser. Nos. 11/242,815; 10/907,472; 11/222,288 and 10/817,612.

FIELD OF THE INVENTION

The present invention relates to a means for supplying respiratory gas under positive pressure, and more specifically, to an improved mask seal interface for covering a breathing passage.

BACKGROUND

Sleep apnea is a condition that occurs when a person regularly stops breathing for ten seconds or longer during sleep. It is a form of sleep-disordered breathing. The severity of sleep apnea can be classified according to the number of times per hour a person stops breathing (apnea) or has slowed breathing (hyperpnoea). Apnea episodes can happen from five to fifty times an hour.

During an apnea episode, a person's blood oxygen level may drop. Over time, low blood oxygen levels can lead to serious health problems and early death. People who have sleep apnea may be at increased risk for developing high blood pressure (hypertension), high blood pressure in the lungs (pulmonary hypertension), depression, mental impairment, irregular heart rhythms, heart disease, and stroke. They also may have a higher-than-average rate of automobile and work-related accidents.

Sleep apnea usually is caused by a blockage (obstruction) in the nose or mouth. A blockage may be caused by defects in the nose or enlarged tissues in the nose, mouth or throat. About 2-4% of people suffer from sleep apnea and affects all age groups. People who have sleep apnea often (but not always) snore loudly and tend to be sleepy throughout the day. Common symptoms include: tossing and turning during sleep and feeling as through they are suffocating; complaining that they are tired all fo the time; awakening with morning headaches and feeling irritable and not rested; failing asleep at inappropriate times, such as while eating, driving or talking; and having problems doing their jobs. The bed partner of a person with sleep apnea may notice periods when the person stops breathing while sleeping.

A sleep study (polysomnography) is the only way to positively diagnose sleep apnea. For some people who have sleep apnea, losing weight, developing good sleeping habits and avoiding alcohol and sleep medications may cure the condition. However, other people may need to use a breathing device that provides continuous positive airway pressure (CPAP). The CPAP device prevents the airway from closing during sleep. A CPAP device is the most common treatment for sleep apnea. If enlarged tissues are causing the blockage, surgery may be needed.

BIPAP

Bilevel therapy works by delivering two different levels of positive air pressure: a higher level of pressure during inhalation and a lower level of pressure during exhalation. There are a number of conditions for which a physician might prescribe Bipap therapy. Bipap devices provide therapy for people with obstructive sleep apnea (OSA) if they have found CPAP therapy too difficult. Bilevel devices can also provide noninvasive position pressure ventilation (NPPV) for people with respiratory disorders of other forms of sleep-disordered breath (SDB).

The breathing device includes a compressor that delivers air, oxygen or a mixture thereof at a controlled rate to a mask that seals tightly against the patient airway. There are both nasal masks and full face masks available. CPAP manufacturers includes Devilbiss, Fisher & Paykel, Puritan-Bennett, Resmed, Respironics, Med Ind American, Inc. and Viasys. An important feature of the CPAP mask is comfort and sealing characteristics. The patient has to wear the mask at night during his sleep. During sleep the compressor delivers controlled gas pressure to the mask. Because of the pressure of the gas between the face and the mask, a relatively large force is required to keep the mask in place. This retaining force is exerted by the mask "head gear," this is a structure of straps that holds the mask in place. The head gear pushes the mask tightly against the patient's face. Accordingly issues arise relating to comfort and skin adhesion and damage.

Some CPAP masks already commercially available have a seal made of soft elastomers, some have a double structure of an elastomer plus an additional thin film over the elastomer in order to minimize skin breakdown. The surface characteristics of the seal are important. The seal should not grab the skin at all. It should not exert tangential stresses on the skin. The patient is likely to move in his sleep and, therefore, the mask is likely to impinge on the bedding and be subject to lateral stresses. Such stress, if transmitted to the skin, will likely cause skin damage.

SUMMARY OF THE INVENTION

The long-standing but heretofore unfulfilled need for a face-seal interface having enhanced utility in applications involving sustained contact with human skin is now met by a new, useful, and non-obvious invention.

The novel elastomer composition for the face-seal interface for a respiratory mask is formed by mixing together plasticizing oil, preselected additives, and a polymer to form a mixture. The mixture is heated until it becomes molten and the molten mixture is charged into a mold for producing useful items.

The additives are in a stable solution when the mixture is in its molten state. An elastomer is formed when the molten mixture cools and solidifies. As the mixture cools down the solubility of the additives decreases and the mixture becomes a supersaturated solution. When solidification is complete, the additives begin to precipitate from the elastomer. The additives migrate, through the process of diffusion, to the surface of the elastomer where they form a powdery interface with a user's skin. This greatly improves the comfort of the user and enables the elastomer to remain in contact with the user's skin for prolonged periods of time.

The at least one additive may be selected from a group consisting of Tetrakis (2,4-di-tert-butylphenyl) [1,1-biphenyl]-4,4'-diylbisphosphonite; Tris(2,4-ditert-butylphenyl) phosphate; Butanedioic acid, dimethylester, polymer with 4-hydroxy-2,2,6,6-tetramethyl-1-piperidine ethanol; 2,6-di-tert-butyl-4-(4,6-bis(octylthio)-1,3,5-triazin-2-ylamino)phenol; 3,3',3',5,5',5'-hexa-tert-butyl-a,a',a'-(mesitylene-2,4,6-triyl) tri-p-cresol; and Pentaerythritol Tetrakis (3-(3,5-di-tert-butyl-4-hydroxphenyl)propionate).

The plasticizing oil may be heated prior to mixing the additive and polymer therewith, but such heating is not strictly necessary. An extruder, a molding machine, or other similar heated vessel is used to accomplish the above-mentioned melting of the mixture so that the additives become melted and soluble in the molten mixture.

Precipitation of the additives begins after solidification of the elastomer. More particularly, the additives remain dissolved in the molten mixture until the mixture solidifies and becomes an elastomer. Precipitation of the additives from the elastomer begins after the elastomer has cooled and solidified. The additives that precipitate and reach the surface of the elastomer provide a dry layer of microscopic powder on the elastomer surface.

The novel process also produces micro-craters on the surface of the elastomer. Both the powder and the micro-craters reduce friction between the user's skin or other human tissue and the elastomer. Even if the surface is wet, the micro-craters collect small pools of liquid that provide lubricity.

There are several mechanical configurations of the face-seal interface. In a first embodiment, the interface may be molded into a lip seal configuration. In a second embodiment, the elastomer face-seal interface may be molded into a bladder and filled with fluid, gel or particles. The bladder may be filled with particles under negative pressure (vacuum-packed) whereby the bladder conforms to a face when forced on the face yet retains the shape even if the mask is removed. Alternatively, the bladder may be filled by a combination of particles and non-reactive fluid such as water or silicone oil. As the interstitial space between particles is filled with fluid, the filling of the bladder with particles and fluid may be performed at atmospheric pressure.

DETAILED DESCRIPTION OF PREFERRED EMBODIMENT

It should be noted that a sleep apnea mask is only one application of the present invention. Protective goggles, anesthetic masks, nuclear-biologic-chemical protective masks, or any other respiratory device that is sealingly fit to the breathing pathway of an individual is anticipated by the present invention.

As used herein, the term "elastomers" refers to materials having attributes similar to gels. One important attribute of a gel is that its physical state is normally neither a liquid nor a solid. Gels do not seek to fill a container and do not necessarily have a level surface. Gels keep their own shape when they are subjected to gravity. Gels self-heal when cut, have substantially no resistance to traction, and have substantially no elongation.

Examples of true gels are the gels used in food gelatins, wound care, and lubricants. In the present disclosure, triblock polymers, when mixed with plasticizing oils, produce elastomers that exhibit good mechanical properties, including elongation, tear and tensile strength characteristics.

Figure 1:
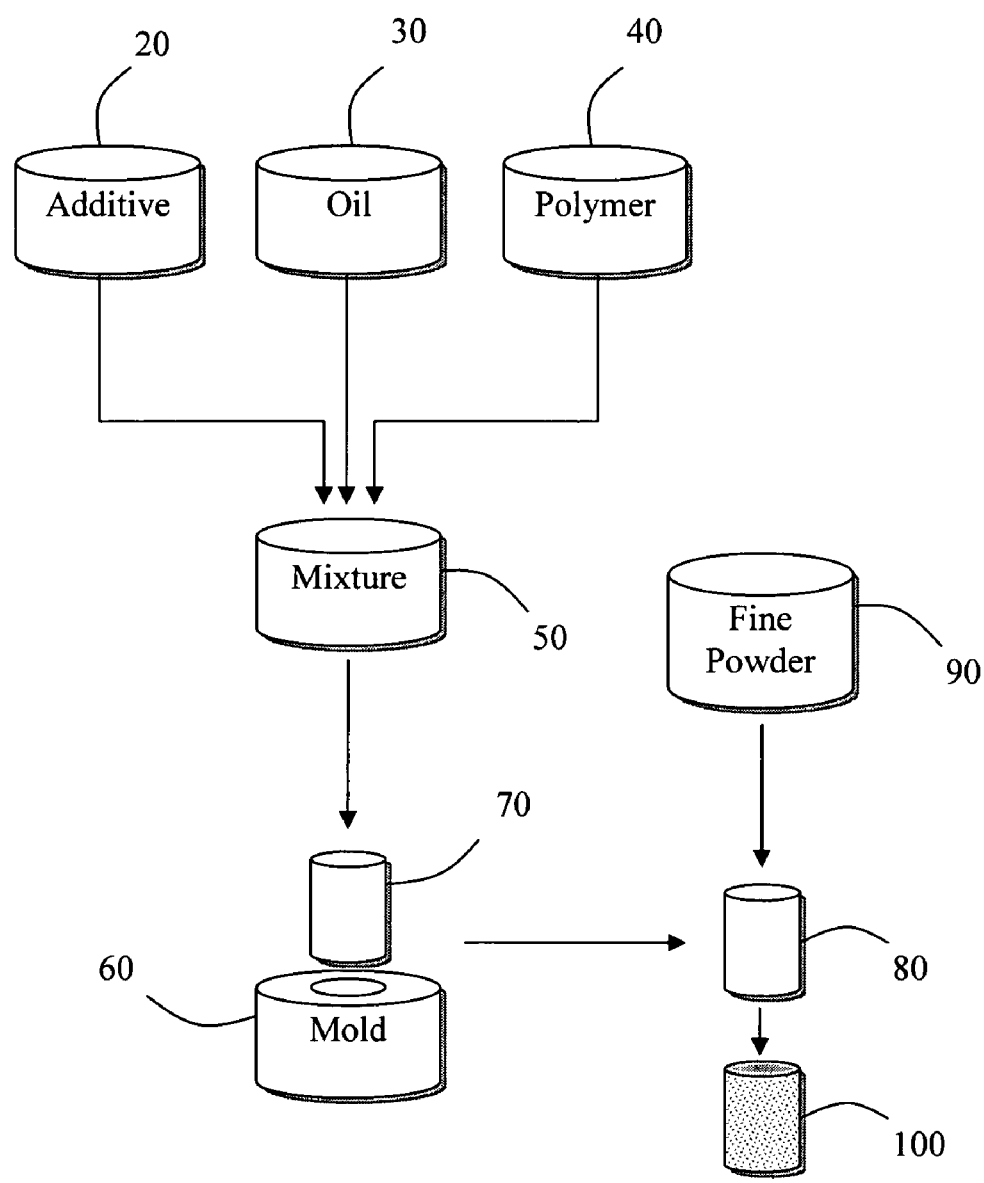
FIG. 1 is a diagrammatic view of a method of manufacturing the elastomer according to the invention.

Turning to FIG. 1, the novel process of making an elastomer includes the steps of mixing additive 20, plasticizing oil 30, and polymer 40 to form mixture 50. Plasticizing oil 30 may be heated prior to the addition of additive 20 and polymer 40 thereto, but such heating is not critical to the invention. Mixture 50 is melted in an extruder, a molding machine or other suitable heated vessel so that the additives become soluble in molten mixture 50 and remain in stable solution in the molten mixture. Molten mixture 50 is molded into the form of a useful item in mold 60 at an appropriate temperature. When allowed to cool, the mixture solidifies and forms elastomer 80. The additives begin to diffuse to the surface of the elastomer upon completion of the solidification process. Precipitation may be initiated by seeding the surface of the elastomer 80 with some powder 90 such as talcum powder. Elastomer 80 is cooled to solidified elastomer 100 whereby the additive 20 precipitates to the surface of solidified elastomer 100 in the form of dry powder.

If the plasticizing oil is heated, the appropriate temperature range is about 130 to 165° F. Plasticizing oils such as paraffinic oils, naphtenic petroleum oils, mineral oils, and synthetic liquid oilgomers of polybutene, polypropylene, polyterpene, etc. may be used. Optionally, a seeding of the oil may also be effected, with an insoluble fine powder such as talc. Preferably, 300 to 1000 parts by weight of the plasticizing oil may be used.

The additive is mixed in the plasticizing oil, optionally with seed, for approximately 10 minutes at 130 to 165° F. The additive may also be added to the plasticizing oil with or after the addition of the polymer. Table I discloses suitable additives.

TABLE 1

| | Chemical Name |
|---|---|
| 1 | Tetrakis (2,4-di-tert-butyiphenyl) [1,1-biphenyl]-4,4'-diylbisphosphonite |

TABLE 1-continued

| | Chemical Name |
|---|---|
| 2 | Tris (2,4-ditert-butylphenyl) phosphate |
| | Butanedioic acid, dimethylester, polymer with 4-hydroxy-2,2,6,6-tetramethyl-1-piperidine ethanol |
| 4 | 2,6-di-tert-butyl-4-(4,6-bis(octylthio)- 1,3,5-triazin-2-ylamino) phenol |
| 5 | 3,3',3',5,5',5'-hexa-tert-butyl-a,a',a'-(mesitylene-2,4,6-triyl) tri-p-cresol |
| 6 | Pentaerythritol Tetrakis (3-(3,5-di-tert-butyl-4-hydroxphenyl)-propionate) |
| 7 | Phenol, 2-(5-chloro-2H-benzotriazole-2-yl)-6-(1,1-dimethylethyl)-4-methyl |
| 8 | Thiodiethylene bis[3-(3,5-di-tert-butyl-4-hydroxyphenyl)propionate} |
| 9 | Calcium phosphonate |
| 10 | Dioctadecyl 3,3'-thiodipropionate |
| 11 | Didodecyl 3,3'-thiodipropionate |
| 12 | 2-(1,1-dimethylethyl)-6-[[3-(1,1-dimethylethyl)-2-hydroxy-5-methylphenyl] methyl-4-methylphenyl acrylate |
| 13 | N,N'-hexane-1,6-diylbis(3-(3,5-di-tert-butyl-4-hydroxyphenylpropionamide)) |

The tris(2,4-ditert-butylphenyl)phosphate as listed in Table I is a white crystalline powder, commonly used as a phosphate processing stabilizer for polycarbonate and polyolefins. It is typically used in combination with phenolic antioxidants and acts for synergistical color stability and polymer viscosity. The butanedionic acid as listed in Table I, also known as succinic acid, is a dicarboxylic acid with four carbon atoms, occurs naturally in plant and animal tissues and plays a significant role in intermediary metabolism (Krebs cycle). It is a colorless crystalline solid with a melting point of 185-187° C., soluble in water, slightly dissolved in ethanol, ether, acetone and glycerine, but not dissolved in benzene, carbon sulfide, carbon tetrachloride and oil ether. The common method of synthesis of succinic acid is the catalytic hydrogenation of maleic acid or its anhydride. Succinic acid has uses in certain drug compounds, in agricultural and food production, and in perfume esters.

Preferably, 0.5 to 10 parts of one or more additives is mixed with the plasticizing oil or with the plasticizing oil and polymer mixture. The additives are solid at room temperature (25° C.) and soluble in the molten mixture. The additives have higher solubility in the triblock copolymer elastomers at higher temperatures than at room temperatures. The addition of such additives is in a predetermined proportion that exceeds the solubility of the additives in the elastomer at room temperature. The addition of such additives to the mixture of polymers and plasticizing oil is made either prior to the melting of the mixture in a heated vessel or when the mixture is in its molten state.

A polymer or mixture of polymers is added to the plasticizing oil or to the mixture of plasticizing oil and additives for 30 minutes at 140° F. to 165° F. starting temperature. The polymers may be of the type poly(styrene ethylene ethylene propylene styrene) (SEEPS), poly(styrene ethylene butylenes styrene) (SEBS), or poiy (styrene ethylene propylene styrene) (SEPS). These polymers are sold under the trademarks Septon® and Kapton®. Preferably, 100 parts by weight of one or a mixture of two or more of a hydrogenated styrene/isoprene/butadiene block copolymer are used.

The mixture containing the plasticizing oil, the additive and the polymer is melted in an extruder, a reciprocating screw molding machine, or a heated vessel at about 415° F. As mentioned earlier, the additive may be added to the mixture of polymers and plasticizing oils either prior to the melting of the mixture or in the melt phase.

After melting, the mixture is maintained at an elevated temperature, with or without mixing, for an amount of time necessary to ensure adequate dissolution and dispersion of the additives in the mixture. After the expiration of such amount of time, the mixture is allowed to cool or is actively cooled. In either event, the mixture undergoes a phase change from liquid to solid. The additives remain dissolved in the molten mixture, but upon solidification of the mixture, the mixture becomes an elastomer and precipitation of the additives from the elastomer begins.

More particularly, where the mixture is first melted and then cooled, at a controlled temperature profile, precipitation of the additives occurs within the elastomer as the solubility parameters of the additive in the elastomer are exceeded. The solubility of the additives decreases as the temperature of the elastomer falls. Precipitation may be initiated by seeding the surface of the elastomer with a fine powder such as talcum powder. Precipitation may also be initiated by mechanical solicitation of the elastomer, such as stretching or other deformation of the elastomer.

The size of the particles of the precipitated phase is a function of the time temperature profile maintained during the cooling period and of the mechanical stress to which the elastomer is subjected. More particularly, the particles increase in size as the cooling rate is decreased and as the amount of mechanical deformation is decreased. A faster cooling rate and greater mechanical deformation produces smaller particle sizes.

The diffusion rate of precipitate to the surface of the elastomer also increases as the stress to strain ratio decreases, i.e., the diffusion rate increases as the modulus of the elastomer, or elastic limit stress, decreases.

Molding, casting or extruding of the molten mixture is preferably conducted at a mold temperature of 95-130° F. for 5-10 minutes. The molded elastomer is removed from the mold after the expiration of such period of time. Although stretching is not required, stretching of the elastomer by about 50% will improve the diffusion rate. Other mechanical deformation of the elastomer may be substituted for or added to the stretching.

A precipitation seed such as talcum powder may also be applied to the surface of the molded part.

The step of aging at a controlled temperature profile may also be performed. The aging may be accomplished at a temperature of 20-32° F. for one (1) hour.

The precipitated phase diffuses to the surface of the elastomer and collects as a powder on its surface. After removal of the surface powder, by wiping, washing, or the like, additional powder migrates to the surface. The process is repeated until the saturation level at room temperature of the precipitate phase in the elastomer is reached. The process of diffusion to the surface then stops.

Figure 2:
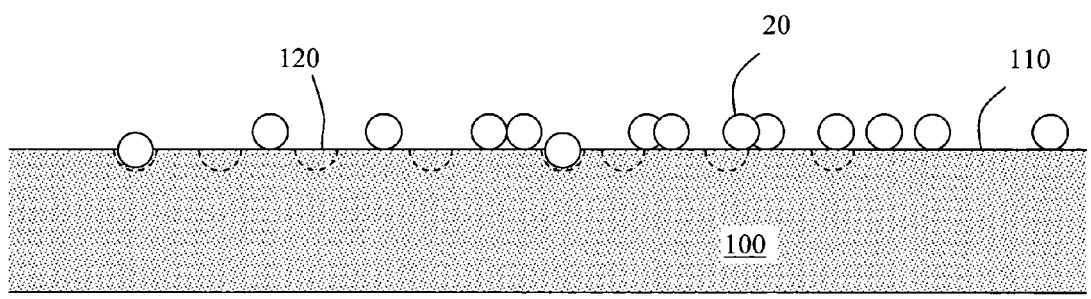
FIG. 2 is a side-elevated, partially sectional diagrammatic view of the elastomer surface according to an embodiment of the invention.

As illustrated in FIG. 2, the diffusion has several advantageous characteristics. The diffused precipitated phase modifies the surface characteristics of elastomer 100 by creating micro-craters 120 on elastomer surface 110.

Figure 5:
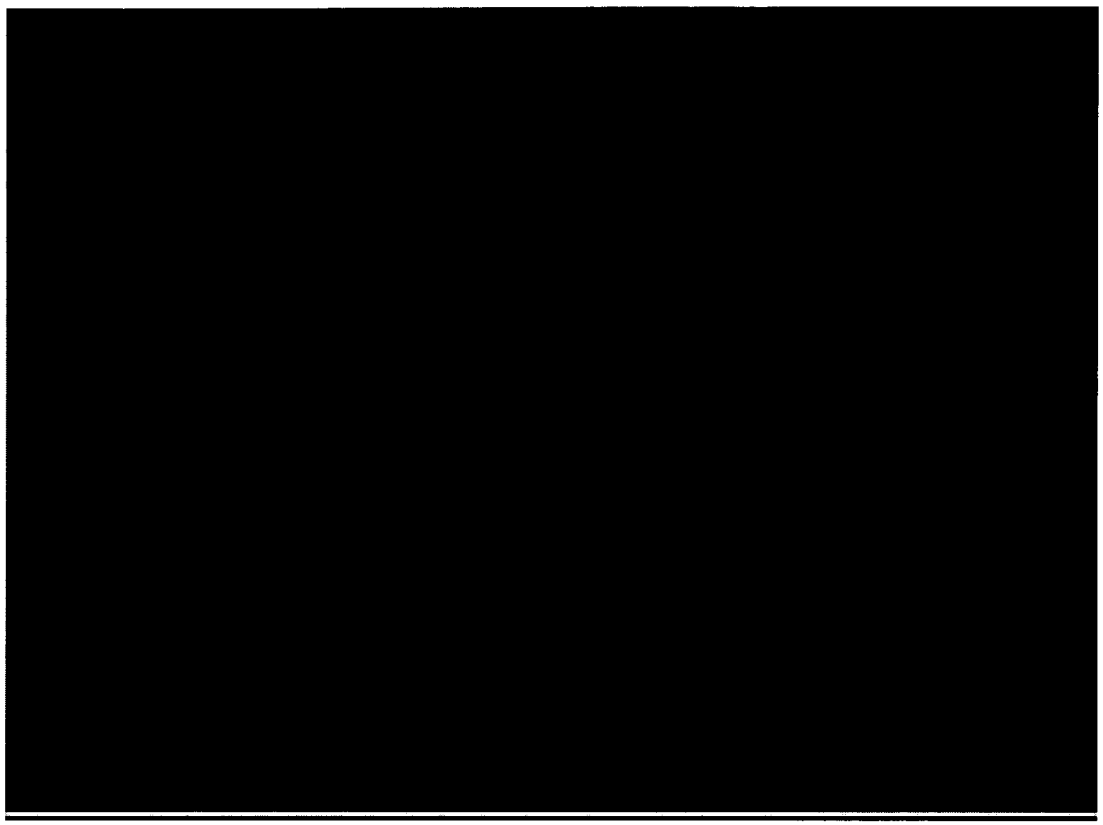
FIG. 5 is a photograph of the modified surface as molded with a 50× magnification.
Figure 6:
FIG. 6 is a photograph of the modified surface during the cooling period with a 50× magnification.

The diffusion has several advantageous characteristics. The diffused precipitated phase modifies the surface characteristics of the elastomers by creating micro-craters on the surface as seen in FIG. 5. The photo shows a 50× magnification of a molded surface, which is shiny to the eye and "grabby" to the touch. FIG. 6 shows a 50× magnification of the surface during the cooling period where the surface is dull to the eye and smooth to the touch.

Figure 7:
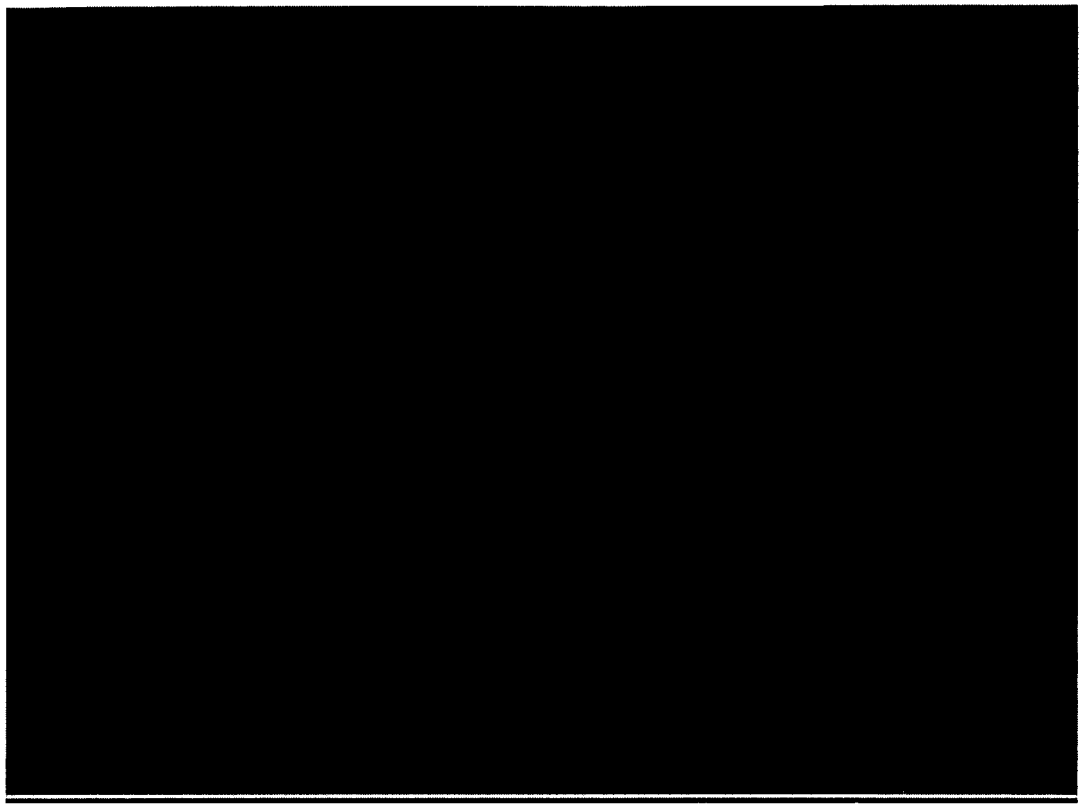
FIG. 7 is a photograph of the modified surface after an appropriate cooling period with a 50× magnification.
Figure 8:
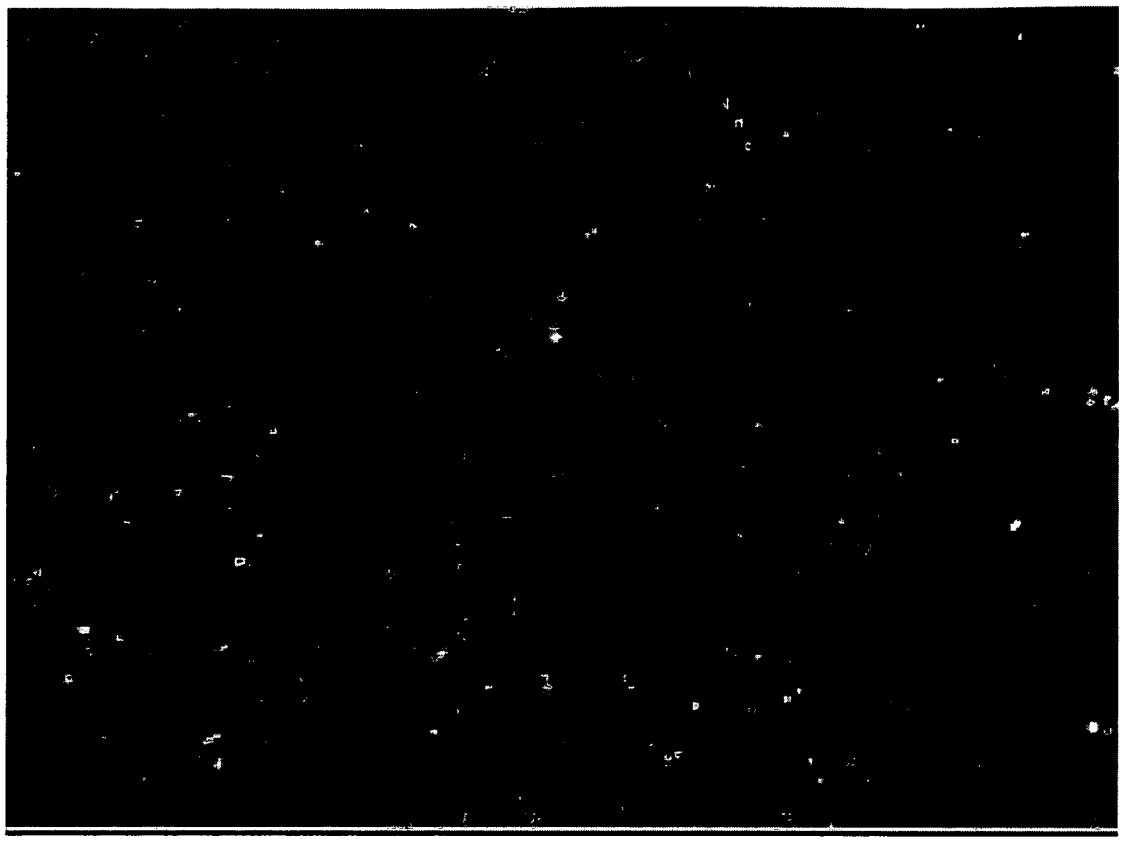
FIG. 8 is a photograph of the modified surface after an inappropriate cooling period with a 50× magnification.

A second advantage to the diffusion is that this process modifies the surface characteristics of the elastomer by providing a dry layer of microscopic powder. As seen in FIG. 7, after an appropriate cooling period, the surface is powdery to the eye and to the touch. As indicated in FIG. 8, after an inappropriate cooling period, the surface is rough to the touch and an excessive amount of powder is visible to the eye.

Figure 3:
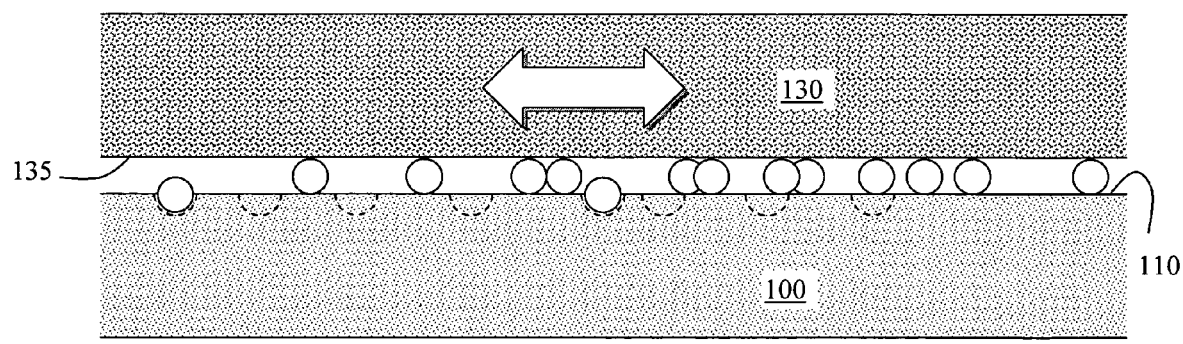
FIG. 3 is a side-elevated, partially sectional diagrammatic view of the elastomer surface in contact with an epidermal surface according to an embodiment of the invention.
Figure 4:
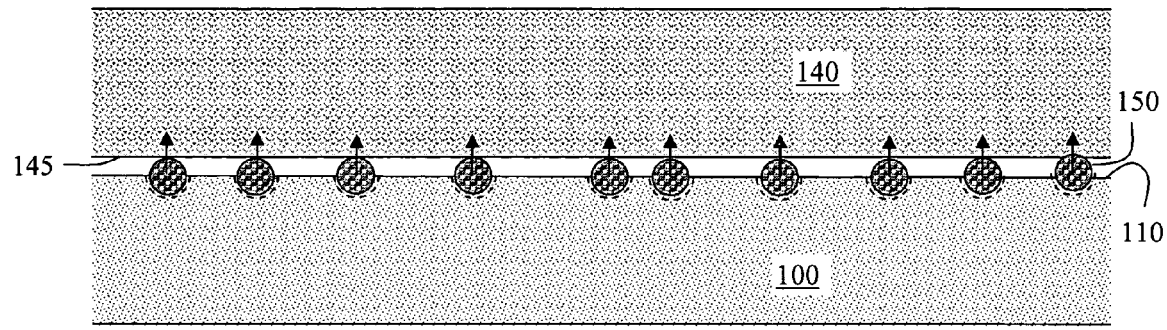
FIG. 4 is a side-elevated, partially sectional diagrammatic view of the elastomer surface illustrating the migration of compounds from the surface of the elastomer to overlaying tissue according to an embodiment of the invention.

The surface modifications achieved by the novel method reduce the friction between the skin or other human tissue and the elastomer. In FIG. 3, epidermal tissue 130 having skin surface 135 abuts molded surface 110 whereby precipitated additive 20 reduces lateral movement friction. Thus a lubricant may be added to molded surface 110 and retained by micro-craters 120 prior to contact with epidermal tissue 130. This is an advantageous feature in CPAP mask applications and other medical masks.

Figure 9:
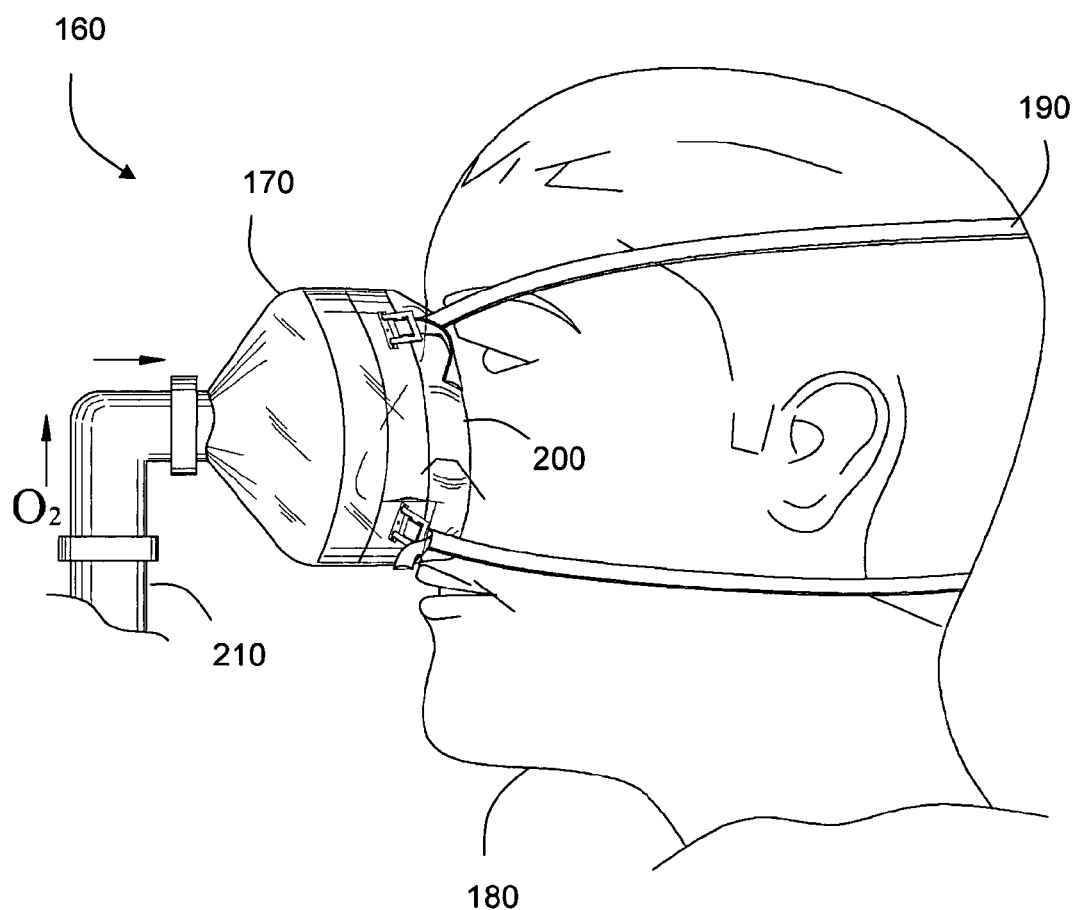
FIG. 9 is a side elevation view of a CPAP mask strapped to the head of a wearer.

In FIG. 9, a generic configure 160 is shown for a nasal sleep apnea mask. Although the mask is shown as a nasal cup, masks that cover the mouth and nose of the wearer are also anticipated. Nasal cup 170 is secured to wearer 180 by straps 190. A plenum is created by a pressurized fluid conduit 210. As the seal of cup 170 is important, straps 190 are pulled tight and bias face-seal interface 200 against the face of wearer 180.

Figure 10A:
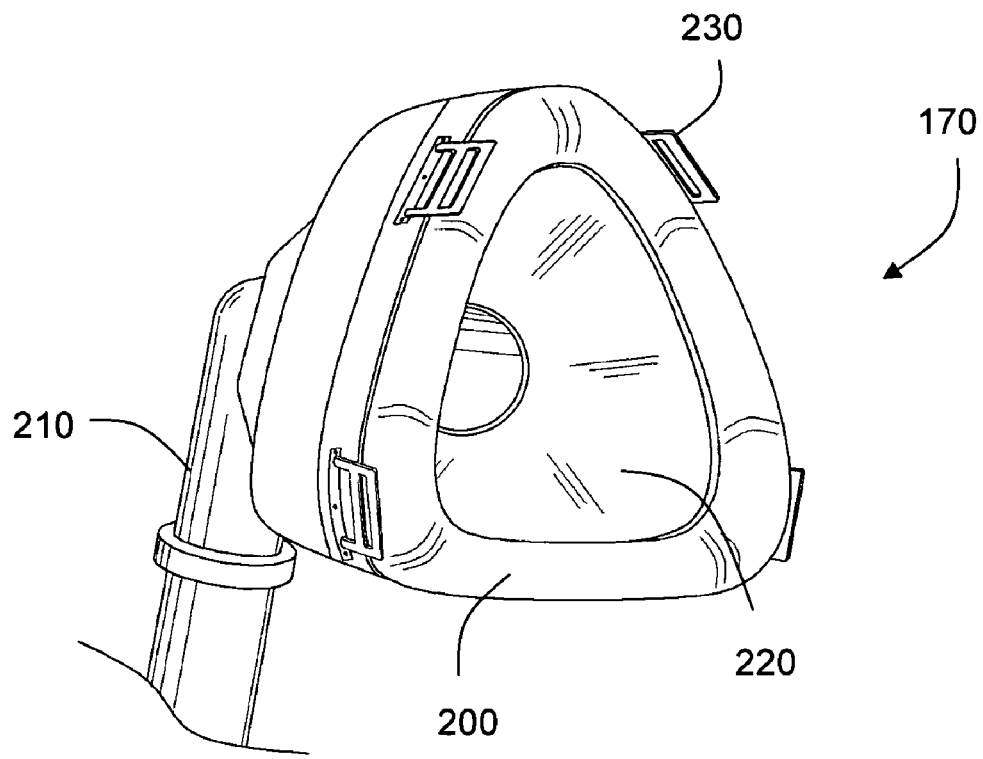
FIG. 10A is an elevated, isometric view of an embodiment of the invention having a face seal interface of homogenous composition.
Figure 10B:
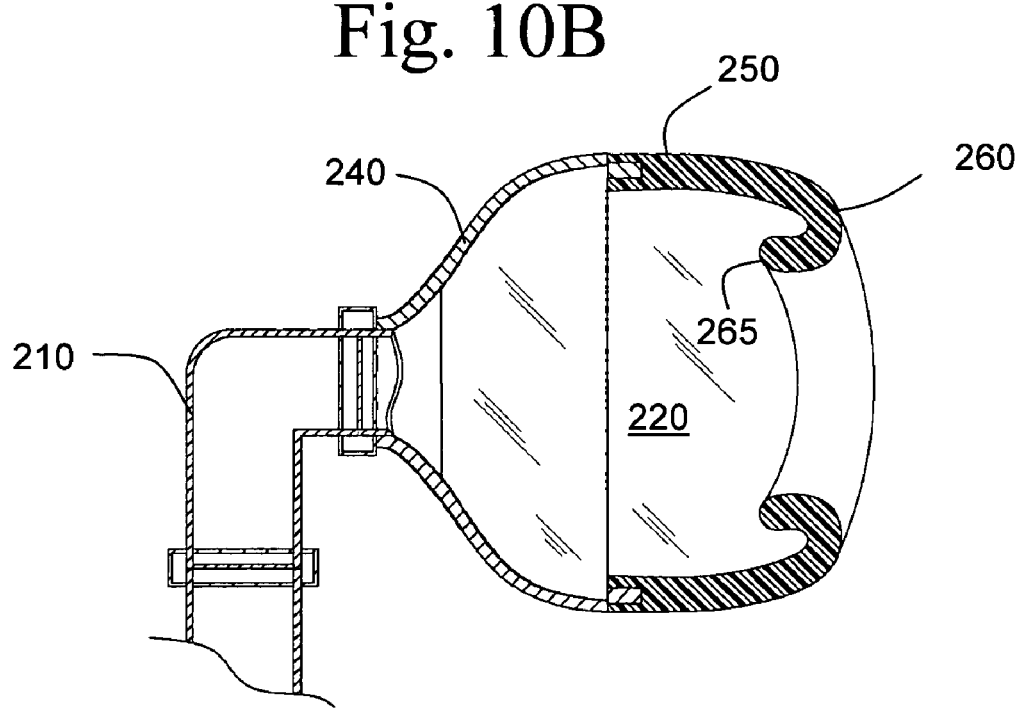
FIG. 10B is a sectional view of an embodiment of the invention having a face seal interface of homogenous composition.

The simplest configuration of a CPAP Mask seal is the one shown in FIGS. 10A-B, where the elastomer with modified surface characteristics is shaped as a lip seal 265. FIG. 10A shows strap bracket 230 for attaching straps 190 to nasal cup 170. Mask interior 220 is pumped with air or an air mixture from fluid conduit 210 to form a plenum. Face-seal interface 200 is biased against the face of wearer 180.

FIG. 10B shows a first embodiment of the invention wherein the elastomer forms lip seal 265. Elastomer forms solid wall 250 which extends from rigid support 240 to face-seal interface 200.

Figure 11A:
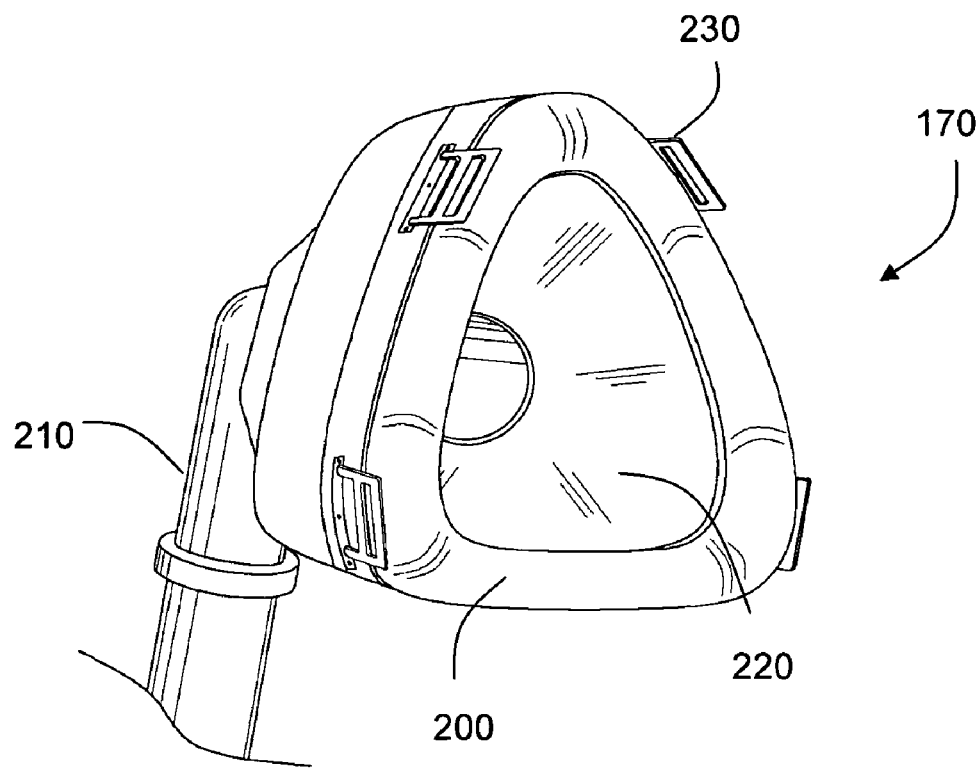
FIG. 11A is an elevated, isometric view of an embodiment of the invention having a face seal interface comprising a gel-filled elastomeric bladder.
Figure 11B:
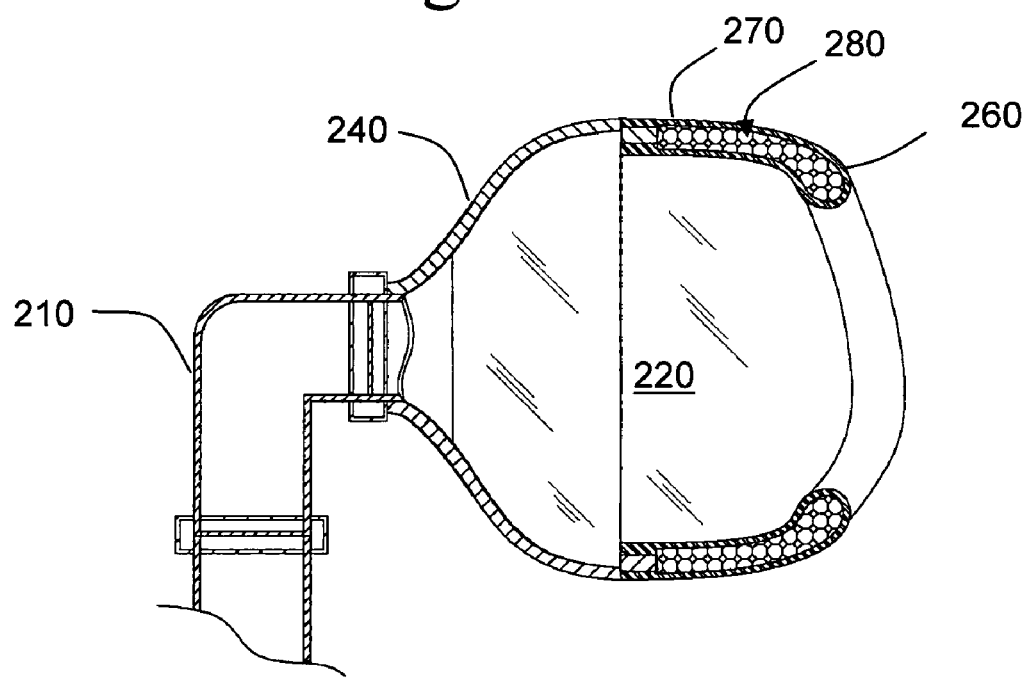
FIG. 11B is a sectional view of an embodiment of the invention having a face seal interface comprising a gel-filled elastomeric bladder.

A geometry that is more comfortable to the patient is the one shown in FIGS. 11A-B, where the surface modified elastomer provides only the outer bladder portion 270 of a seal that consists of a bladder filled with gel 280. By controlling the consistency of the gel the bladder can be made to conform to the patients face with a minimum of force on the part of the head gear.

Figure 12A:
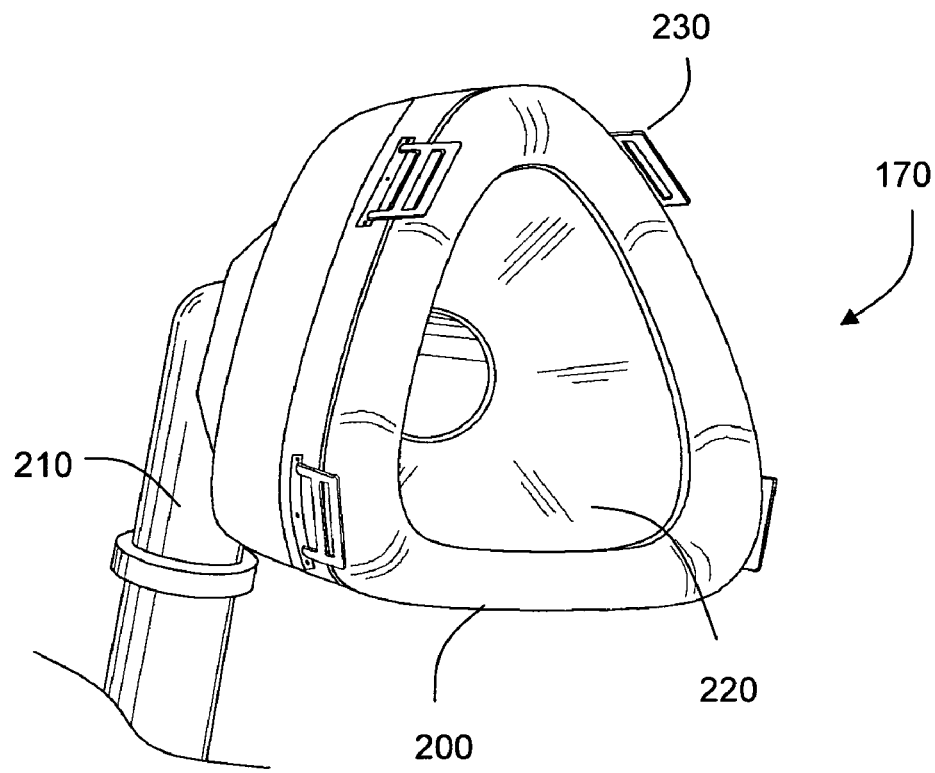
FIG. 12A is an elevated, isometric view of an embodiment of the invention having a face seal interface comprising a particle-filled elastomeric bladder.
Figure 12B:
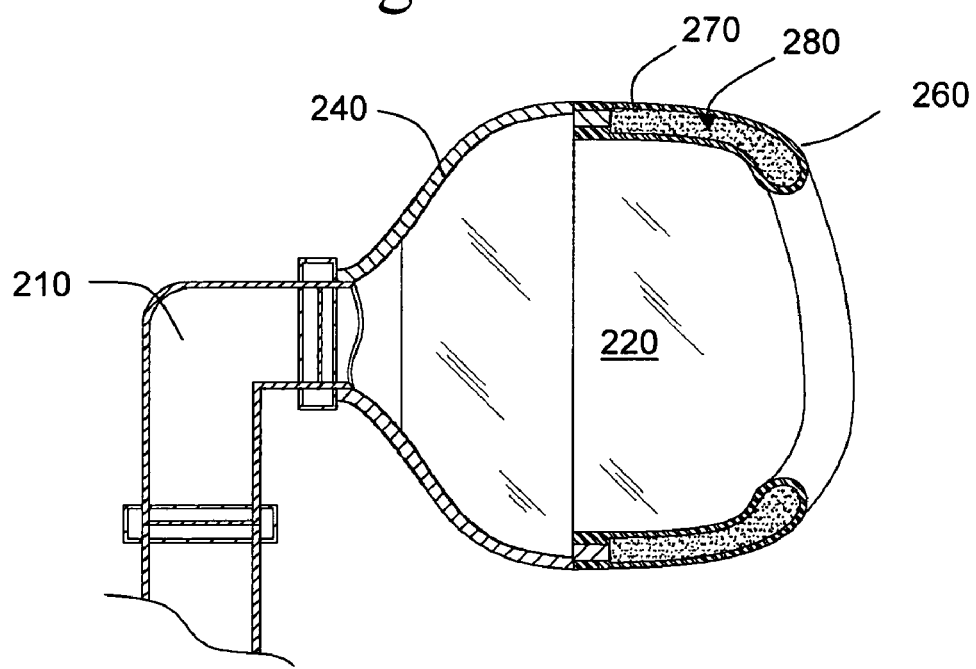
FIG. 12B is a sectional view of an embodiment of the invention having a face seal interface comprising a particle-filled elastomeric bladder.

Another configuration for the seal construction is shown in FIGS. 12A-B including bladder 270 made of the modified surface elastomer. Bladder 270 is filled with lose fine powder 280 made of solid or hollow particles (FIG. 12B).

In a preferred embodiment the particles can be placed in the bladder, under negative atmospheric pressure (vacuum) in order to provide a face conforming shape to the bladder when forced on to the patients face, this shape is retained even if the mask is removed from the patient. The bladder, that is, takes a set, which can be reconfigured again and again over the face of the patient.

In another embodiment the particles are in the bladder at atmospheric pressure and lubrication of the particles can be provided by the addition of a fluid compatible with the material, such as water or silicone oil.

What is claimed is:

1. A method of manufacturing a face-seal interface for a respiratory facemask, said interface configured and adapted to provide a seal between peripheral boundaries of said respiratory facemask and a patient's face, and wherein said interface has a micro-cratered outer surface and is covered with a dry powder acting as a lubricant; said method comprising the steps of:

mixing together plasticizing oil and a polymer to form an elastomeric polymer, and mixing said elastomeric polymer with a predetermined amount of at least one additive to form a mixture, wherein the predetermined amount of the at least one additive is proportionately in excess of an amount of additive that is soluble in the mixture at room temperature;

heating the mixture to at least a melting point where the mixture becomes molten and the additive is soluble in the molten mixture in a stable solution;

molding or extruding the mixture to form said interface configured and adapted to provide a seal between peripheral boundaries of said respiratory facemask and a patient's face;

allowing the mixture to cool until it solidifies and becomes an-elastomer in the form of said interface;

whereby the at least one additive precipitates after the solidification of the elastomer; and whereby the at least one additive migrates to the surface of the elastomer to form a dry powder that covers the surface of the face-seal interface thereby providing a lubricant and further, creates micro-craters on the surface of the face-seal interface, whereby both the powder and micro-craters reduce friction between the user's skin and the elastomer.

2. The method of claim 1, wherein the at least one additive is added to the mixture of polymer and plasticizing oil when the mixture is ion its molten state.

3. The method of claim 1, further comprising the step of stretching the elastomer after the elastomer has solidified.

4. The method of claim 1, further comprising the step of mixing a seed oil with an insoluble fine powder to the plasticizing oil.

5. The method of claim 1, further comprising the step of posting a precipitation seed on the molded elastomer.

6. The method of claim 1, further comprising the step of selecting the at least one additive from the group consisting of Tetrakis (2,4-di-tert-butylphenyl) [1,1-biphenyl]-4,4'-diyl-bisphosphonite; Tris(2,4-di-tert-butylphenyl)phosphate; Butanedioic acid, dimethylester, polymer with 4-hydroxy-2,2,6,6-tetramethyl-1-piperidine ethanol; 2,6-di-tert-butyl-4-(4,6-bis(octylthio)-1,3,5-triazin-2-ylamino)phenol; 3,3',3',5,5',5'-hexa-tert-butyl-a,a',a'-(mesitylene-2,4,6-triyl) tri-p-cresol; and Pentaerythritol Tetrakis (3-(3,5-di-tert-butyl-4-hydroxphenyl)propionate).

7. The method of claim 1, further comprising the step of selecting the polymer from a group consisting of poly(styrene ethylene propylene styrene), poly(styrene ethylene butylene styrene), and poly(styrene ethylene propylene styrene).

8. The method of claim 1, further comprising the step of molding the elastomer face-seal interface into a lip seal configuration.

9. The method of claim 1, further comprising the step of molding the elastomer face-seal interface into a gel-filled bladder.

10. The method of claim 1, further comprising the step of molding the elastomer face-seal interface into a particle-filled bladder.

11. The method of claim 10, further comprising the step of filling-the bladder with particles under negative pressure whereby the bladder conforms to a face when forced on the face yet retains the shape even if the mask is removed.

12. The method of claim 10, further comprising the step of filling the bladder with particles and fluid in combination.

13. The method of claim 12, wherein the step of filling the bladder with particles and fluid in combination is performed substantially at atmospheric pressure.

14. The method of claim 12 wherein the fluid is selected from the group consisting of water and silicone oil.

15. A face-seal interface for a respiratory mask configured and adapted to provide a seal between peripheral boundaries of said respiratory facemask and a patient's face made by the method of claim 1 thereby having a micro-cratered outer surface covered with a dry powder acting as a lubricant.

16. The face-seal interface of claim 15, wherein the additive is from the group consisting of Tetrakis (2,4-di-tert-butylphenyl) [1,1-biphenyl]-4,4'-diylbisphosphonite; Tris(2,4-di-tert-butylphenyl)phosphate; Butanedioic acid, dimethylester, polymer with 4-hydroxy-2,2,6,6-tetramethyl-1-piperidine ethanol; 2,6-di-tert-butyl-4-(4,6-bis(octylthio)-1,3,5-triazin-2-ylamino)phenol; 3,3',3',5,5',5'-hexa-tert-butyl-a,a',a'-(mesitylene-2,4,6-triyl) tri-p-cresol; and Pentaerythritol Tetrakis (3-(3,5-di-tert-butyl-4-hydroxphenyl)propionate).

17. The face-seal interface of claim 15, wherein the polymer is selected from a group consisting of poly(styrene ethylene propylene styrene), poly(styrene ethylene butylene styrene), and poly(styrene ethylene propylene styrene).

18. A face-seal interface for a respiratory mask as defined in claim 15 wherein said face-seal interface comprises an elastomeric bladder.

19. The face-seal interface of claim 18 wherein the elastomeric bladder is packed filled with the particles.

20. The face-seal interface of claim 19 wherein the interstitial space between particles within the elastomeric bladder is filled with fluid.

21. The face-seal interface of claim 20 wherein the fluid is selected from the group consisting of water and silicone oil.

22. The face-seal interface of claim 19 wherein the particles are vacuum packed into the elastomeric bladder.

* * * * *